United States Patent
Mulrooney et al.

(10) Patent No.: US 12,059,537 B2
(45) Date of Patent: Aug. 13, 2024

(54) SAFETY CLASP AND GARMENT CLIP

(71) Applicant: Phagenesis Limited, Manchester (GB)

(72) Inventors: Conor Mulrooney, Manchester (GB); Andrew Matthews, Fittleworth (GB); Nicholas John Smart, Fittleworth (GB)

(73) Assignee: Phagenesis Limited, Manchester (GB)

( * ) Notice: Subject to any disclaimer, the term of this patent is extended or adjusted under 35 U.S.C. 154(b) by 193 days.

(21) Appl. No.: 17/594,245

(22) PCT Filed: Apr. 9, 2020

(86) PCT No.: PCT/GB2020/050934
§ 371 (c)(1),
(2) Date: Oct. 7, 2021

(87) PCT Pub. No.: WO2020/208366
PCT Pub. Date: Oct. 15, 2020

(65) Prior Publication Data
US 2022/0176077 A1  Jun. 9, 2022

(30) Foreign Application Priority Data
Apr. 11, 2019  (GB) ..................... 1905156

(51) Int. Cl.
*A44B 9/12*    (2006.01)
*A45F 5/02*    (2006.01)
(Continued)

(52) U.S. Cl.
CPC ............. *A61M 25/02* (2013.01); *A44B 9/12* (2013.01); *A45F 5/02* (2013.01); *A61J 15/0053* (2013.01);
(Continued)

(58) Field of Classification Search
CPC ............ A61M 25/02; A61M 2025/024; A61M 2025/028; A61M 2025/0206; A44B 9/12;
(Continued)

(56) References Cited

U.S. PATENT DOCUMENTS 803,464 A    10/1905  Beck
1,032,436 A   7/1912  Smith
(Continued)

FOREIGN PATENT DOCUMENTS

CN    203389196 U    1/2014
CN    203954394 U   11/2014
(Continued)

OTHER PUBLICATIONS

Bath et al., Pharyngeal electrical stimulation for neurogenic dysphagia following stroke, traumatic brain injury or other causes: Main results from the PHADER cohort study, EClinical Medicine 28 (2020) 100608, 9 pages.
(Continued)

*Primary Examiner* — Robert Sandy
(74) *Attorney, Agent, or Firm* — Fortem IP LLP

(57) ABSTRACT

Various embodiments of the present technology are directed to a safety clasp (10) including a clasp base (22); a securing element (32) with a sharp end (33), a piercing section (34) and a support (36); and a clasp body (12) including first and second body sections (12A, 12B) and a recess (13) defined therebetween, the body being adjustable relative to the clasp base and the securing element such that in an open configuration the recess is clear and only the first body section houses the sharp end and in a closed configuration the piercing section bridges the recess and only the second section houses the sharp end. Various embodiments of the present technology are directed to a garment clip (100) including such a safety clasp.

20 Claims, 9 Drawing Sheets

(51) Int. Cl.
*A61J 15/00* (2006.01)
*A61M 25/02* (2006.01)

(52) U.S. Cl.
CPC ............... *A61M 2025/0206* (2013.01); *A61M 2025/024* (2013.01); *A61M 2025/028* (2013.01)

(58) Field of Classification Search
CPC .......... A44B 9/16; A45F 5/02; A61J 15/0053; Y10T 24/46; Y10T 24/1365; Y10T 24/1394
See application file for complete search history.

(56) References Cited

U.S. PATENT DOCUMENTS

| | | | |
|---|---|---|---|
| 2,592,506 A * | 4/1952 | Yanagihara | A44B 9/14 24/710.3 |
| 2,627,096 A | 2/1953 | Alessi | |
| 2,779,985 A | 2/1957 | Turner et al. | |
| 3,136,015 A * | 6/1964 | Gunderson | A41F 1/00 24/710.3 |
| 3,179,995 A | 4/1965 | Hawk | |
| 3,225,404 A * | 12/1965 | Gunderson | A41F 1/00 24/710.3 |
| 3,630,195 A | 12/1971 | Santomieri | |
| 3,839,841 A | 10/1974 | Amplatz | |
| 3,894,706 A | 7/1975 | Mizusawa | |
| 3,951,136 A | 4/1976 | Wall | |
| 4,025,015 A | 5/1977 | Kolic | |
| 4,295,618 A | 10/1981 | Morota et al. | |
| 4,453,545 A | 6/1984 | Inoue | |
| 4,691,883 A | 9/1987 | Kurihara | |
| 4,707,906 A | 11/1987 | Posey | |
| 4,776,349 A | 10/1988 | Nashef et al. | |
| 4,840,337 A | 6/1989 | Zaugg | |
| 5,109,870 A | 5/1992 | Silny et al. | |
| 5,147,315 A | 9/1992 | Weber | |
| 5,179,952 A | 1/1993 | Buinevicius et al. | |
| 5,372,131 A | 12/1994 | Heinen | |
| 5,382,239 A | 1/1995 | Orr et al. | |
| 5,389,074 A | 2/1995 | Parker et al. | |
| 5,457,852 A | 10/1995 | Liu | |
| 5,546,938 A | 8/1996 | McKenzie | |
| 5,551,953 A | 9/1996 | Lattin et al. | |
| 5,588,424 A | 12/1996 | Insler et al. | |
| 5,755,225 A | 5/1998 | Hutson | |
| 5,762,638 A | 6/1998 | Shikani et al. | |
| 5,800,402 A | 9/1998 | Bierman | |
| 5,833,663 A | 11/1998 | Bierman et al. | |
| 5,836,895 A | 11/1998 | Ramsey | |
| 5,957,968 A | 9/1999 | Belden et al. | |
| 6,006,138 A | 12/1999 | Don | |
| 6,148,222 A | 11/2000 | Ramsey | |
| 6,259,938 B1 | 7/2001 | Zarychta et al. | |
| 6,266,548 B1 | 7/2001 | Lamade et al. | |
| 6,366,813 B1 | 4/2002 | DiLorenzo | |
| 6,464,697 B1 | 10/2002 | Edwards et al. | |
| 6,484,053 B2 | 11/2002 | Leelamanit et al. | |
| 6,611,699 B2 | 8/2003 | Krueger | |
| 6,613,025 B1 | 9/2003 | Palasis | |
| 6,658,294 B1 | 12/2003 | Zadeh et al. | |
| 6,804,866 B2 | 10/2004 | Lemke et al. | |
| 6,856,822 B2 | 2/2005 | Larsson | |
| 7,324,851 B1 | 1/2008 | DiLorenzo | |
| 7,918,828 B2 | 4/2011 | Lundgaard et al. | |
| 8,048,062 B2 | 11/2011 | Adams et al. | |
| 8,092,433 B2 | 1/2012 | Hamdy | |
| 8,876,798 B2 | 11/2014 | Clark et al. | |
| 9,895,486 B1 | 2/2018 | Carey-Hench | |
| 9,982,742 B2 | 5/2018 | Loewe et al. | |
| 10,285,341 B2 | 5/2019 | McCaslin et al. | |
| 10,743,810 B2 | 8/2020 | Mulrooney | |
| 10,888,690 B2 | 1/2021 | Mulrooney | |
| 2001/0054425 A1 | 12/2001 | Bertram | |
| 2002/0032468 A1 | 3/2002 | Hill et al. | |
| 2002/0065544 A1 | 5/2002 | Smits | |
| 2002/0157673 A1 | 10/2002 | Kessler et al. | |
| 2003/0036794 A1 | 2/2003 | Ragheb et al. | |
| 2004/0034396 A1 | 2/2004 | Asmar et al. | |
| 2004/0220645 A1 | 11/2004 | Kretschmer et al. | |
| 2004/0230162 A1 | 11/2004 | Tan | |
| 2005/0098688 A1 | 5/2005 | Miarka et al. | |
| 2005/0137459 A1 | 6/2005 | Chin et al. | |
| 2005/0146676 A1 | 7/2005 | Silvestro | |
| 2005/0192559 A1 | 9/2005 | Michels et al. | |
| 2005/0229933 A1 | 10/2005 | McGrail et al. | |
| 2006/0085049 A1 | 4/2006 | Cory et al. | |
| 2007/0074728 A1 | 4/2007 | Rea | |
| 2007/0089898 A1 | 4/2007 | Potter | |
| 2007/0156041 A1 | 7/2007 | Rea | |
| 2008/0147013 A1 | 6/2008 | Breton et al. | |
| 2008/0255441 A1 | 10/2008 | Hadani | |
| 2009/0062772 A1 | 3/2009 | Wakeford et al. | |
| 2009/0223698 A1 | 9/2009 | Gilliland et al. | |
| 2009/0255094 A1 | 10/2009 | Reynolds | |
| 2010/0115739 A1 | 5/2010 | Mathur | |
| 2010/0170066 A1 | 7/2010 | Honeycutt | |
| 2010/0206453 A1 | 8/2010 | Leeflang et al. | |
| 2010/0218975 A1 | 9/2010 | Mehan | |
| 2010/0317956 A1 | 12/2010 | Kartush | |
| 2011/0210215 A1 | 9/2011 | Nitsche et al. | |
| 2011/0286217 A1 | 11/2011 | Martinson et al. | |
| 2012/0065469 A1 | 3/2012 | Allyn et al. | |
| 2012/0259208 A1 | 10/2012 | Bloom et al. | |
| 2012/0260921 A1 | 10/2012 | Sangwan | |
| 2013/0006323 A1 | 1/2013 | Tal et al. | |
| 2013/0197321 A1 | 8/2013 | Wilson | |
| 2013/0282078 A1 | 10/2013 | Wacnik | |
| 2014/0012235 A1 | 1/2014 | Pinchuk et al. | |
| 2014/0128936 A1 | 5/2014 | Laufer et al. | |
| 2014/0276663 A1 | 9/2014 | Pinchuk et al. | |
| 2014/0288384 A1 | 9/2014 | Mulrooney | |
| 2014/0378941 A1 | 12/2014 | Su et al. | |
| 2015/0224280 A1 | 8/2015 | Pinchuk et al. | |
| 2017/0224986 A1 | 8/2017 | Imran et al. | |
| 2017/0312497 A1 | 11/2017 | Mulrooney et al. | |
| 2018/0214672 A1 | 8/2018 | Mulrooney | |
| 2018/0235533 A1 | 8/2018 | Mulrooney | |
| 2019/0038894 A1 | 2/2019 | Bassi et al. | |
| 2019/0134380 A1 | 5/2019 | Mulrooney | |
| 2019/0134389 A1 | 5/2019 | Mulrooney | |
| 2020/0061369 A1 | 2/2020 | Mulrooney et al. | |
| 2020/0061370 A1 | 2/2020 | Mulrooney et al. | |
| 2020/0330025 A1 | 10/2020 | Mulrooney | |
| 2021/0077784 A1 | 3/2021 | Mulrooney | |
| 2021/0077808 A1 | 3/2021 | Mulrooney et al. | |
| 2024/0009086 A1 | 1/2024 | Mulrooney | |

FOREIGN PATENT DOCUMENTS

| | | |
|---|---|---|
| CN | 204319485 U | 5/2015 |
| EP | 0510857 A1 | 10/1992 |
| EP | 0571514 A1 | 12/1993 |
| EP | 1179307 A2 | 2/2002 |
| EP | 1047469 B1 | 6/2003 |
| EP | 2253350 A1 | 11/2010 |
| EP | 2693968 A1 | 2/2014 |
| EP | 3331597 A1 | 6/2018 |
| GB | 2169206 A | 7/1986 |
| GB | 2254253 A | 10/1992 |
| GB | 2294642 A | 5/1996 |
| GB | 2313316 A | 11/1997 |
| GB | 2532044 A | 5/2016 |
| GB | 2541039 A | 2/2017 |
| JP | H05115563 A | 5/1993 |
| JP | 2556694 B2 | 11/1996 |
| JP | 2005312969 A | 11/2005 |
| JP | 2008220888 A | 9/2008 |
| JP | 2012512722 A | 6/2012 |
| JP | 2014068716 A | 4/2014 |
| WO | 9400050 A1 | 1/1994 |
| WO | 9405361 A1 | 3/1994 |
| WO | 9526777 A1 | 10/1995 |

(56) References Cited

FOREIGN PATENT DOCUMENTS

| | | |
|---|---|---|
| WO | 9715349 A1 | 5/1997 |
| WO | 9719667 A1 | 6/1997 |
| WO | 9844973 A1 | 10/1998 |
| WO | 03026741 A1 | 4/2003 |
| WO | 2005051472 A2 | 6/2005 |
| WO | 2006024825 A1 | 3/2006 |
| WO | 2009154718 A1 | 12/2009 |
| WO | 2010071812 A1 | 6/2010 |
| WO | 2010091440 A2 | 8/2010 |
| WO | 2012131303 A1 | 10/2012 |
| WO | 2013109835 A1 | 7/2013 |
| WO | 2014152808 A1 | 9/2014 |
| WO | 2015027094 A1 | 2/2015 |
| WO | 2017021727 A1 | 2/2017 |
| WO | 2020183325 A1 | 9/2020 |

OTHER PUBLICATIONS

Bath et al., Pharyngeal Electrical Stimulation for Treatment of Dysphagia in Subacute Stroke A Randomized Controlled Trial, Stroke, Jun. 2016, vol. 47, Issue 6, pp. 1562-1570.

Dziewas et al., Design and implemental of Pharyngeal electrical Stimulation for early de-cannulation in TRACheotomized (PHAST-TRAC) stroke patients with neurogenic dysphagia, International Journal of Stroke, 12(4), 2017, pp. 430-437.

Dziewas et al., PHAryngeal electrical STimulation for early decannulation in TRACheotomised patients with neurogenic dysphagia after stroke (PHAST-TRAC): a prospective, single-blinded, randomised trial, Lancet Neurology, vol. 17, Issue 10, 2018, 29 pages.

Essa et al., The BDNF polymorphism VAL66Met may be predictive of swallowing improvement post pharyngeal electrical stimulation in dysphagic stroke patients, Neurogastroenterol Motil, 2017; 27, 7 pages.

Fraser et al., Differential changes in human pharyngoesophageal motor excitability induced by swallowing, pharyngeal stimulation, and anesthesia, Am J Physiol Gastrointest Liver Physiol, 285: G-137-G144, 2003.

Hamdy et al., The cortical topography of human swallowing musculature in health and disease, Nature Medicine, vol. 2, No. 11, Nov. 1996, pp. 1217-1224.

Hamdy, et al., Long-term reorganization of human motor cortex driven by short-term sensory stimulation, Nature Neuroscience, vol. 1, No. 1, May 1998, pp. 64-68.

Jayasekeran et al., Adjunctive Functional Pharyngeal Electrical Stimulation Reverses Swallowing Disability After Brain Lesions, Gastroenterology, 2010; vol. 138, No. 5, pp. 1737-1746.

Koestenberger, et al., A Pilot Study of Pharyngeal Electrical Stimulation of Orally Intubated ICU Patients with Dysphagia, Neurocrit Care (2020) 32: 532-538.

Magara et al., Tu1254 Does Combining Pharyngeal Electrical Stimulation With Simultaneous Swallowing of Carbonated Liquids Enhance the Cortical Swallowing Motor System?, Gastroenterology, Apr. 2016 [Abstract only].

Magara, et al., Exploring the effects of synchronous pharyngeal electrical stimulation with swallowing carbonated water on cortical excitability in the human pharyngeal motor system, Neurogastroenterol Motil (2016), 11 pages.

Restivo et al., Pharyngeal electrical stimulation device for the treatment of neurogenic dysphagia: technology update, Medical Devices: Evidence and Research, 2018: 11, pp. 21-26.

Restivo et al., Pharyngeal Electrical Stimulation for Dysphagia Associated with Multiple Sclerosis: A Pilot Study, Brain Stimulation 6, 2013, pp. 418-423.

Sasegbon et al., Advances in the Use of Neuromodulation for Neurogenic Dysphagia: . . . , American Journal of Speech-Language Pathology, Jul. 2020, vol. 29, pp. 1044-1064.

Scutt, et al., Pharyngeal Electrical Stimulation for Treatment of Poststroke Dysphagia: Individual Patient Data Meta-Analysis of Randomised Controlled Trials, Stroke Research and Treatment, 2015, 8 pages.

Suntrup et al., Electrical pharyngeal stimulation for dysphagia treatment in tracheotomized stroke patients: a randomized controlled trial, Intensive Care Med (2015) 41: 1629-1637.

Suntrup-Krueger et al., Electrical pharyngeal stimulation increases substance P level in saliva, Neurogastroenterol Motil (2016) 28, pp. 855-860.

Vasant et al., Pharyngeal Electrical Stimulation in Dysphagia Poststroke: A Prospective, Randomized Single-Blinded Interventional Study, Neurorehabilitation and Neural Repair, 2016, vol. 30(9), pp. 866-875.

Gow, David , et al., "Characterising the Central Mechanisms of Sensory Modulation in Human Swallowing Motor Cortex", Clinical Neurophysiology, Elsevier Science, IE, vol. 115, No. 10, Jun. 26, 2004, pp. 2382-2390.

Hamdy, S. , et al., "Modulation of human swallowing behaviour by thermal and chemical stimulation in health and after brain injury", Neurogastroenterol Motil, vol. 15, No. 1, Feb. 2003, pp. 69-77.

Hamdy, Shaheen , et al., "Recovery of Swallowing After Dysphagic Stroke Relates to Functional Reorganization in the Intact Motor Cortex", Gastroenterology, vol. 115, No. 5, Nov. 1998, pp. 1104-1112.

Jasper, Herbert H., "The Ten Twenty Electrode System of the International Federation", Clinical Neurophysiol, vol. 10, pp. 370-375.

Kajii, Yuka , et al., "Sour taste stimulation facilitates reflex swallowing from the pharynx and larynx in the rat", Physiology & Behavior, vol. 77, No. 2-3, 2002, pp. 321-325.

Takeuchi, Hiro-Aki , et al., "Electrophysiological and Behavioral Studies of Taste Discrimination in the Axolotl (Ambystoma mexicanum)", Physiology & Behavior, vol. 56, No. 1, Jul. 1994, pp. 121-127.

Tutuian, R. , et al., "Effects of position on oesophageal function: studies using combined manometry and multichannel intraluminal impedance", Neurogastroenterol Motil., vol. 15, No. 1, Feb. 2003, pp. 63-67.

Wassermann, Eric M., "Risk and safety of repetitive transcranial magnetic stimulation: report and suggested guidelines from the International Workshop on the Safety of Repetitive Transcranial Magnetic Stimulation, Jun. 5-7, 1996", Electroencephalography and clinical Neurophysiology, vol. 108,, 1998, pp. 1-16.

Fraser, Chris et al., Driving Plasticity in Human Adult Motor Cortex is Associated with Improved Motor Function After Brian Injury, Neuron, vol. 34, 831-840, May 30, 2002.

International Search Report and Written Opinion mailed Jul. 20, 2020, International Application No. PCT/GB2020/050934, 11 pages.

* cited by examiner

SAFETY CLASP AND GARMENT CLIP

CROSS-REFERENCE TO RELATED APPLICATION(S)

The present application is a 371 U.S. national phase application of International Application No. PCT/GB2020/050934, filed Apr. 9, 2020, which claims the benefit and priority of United Kingdom Application No. 1905156.4, filed Apr. 11, 2019, which are incorporated herein by reference in their entireties.

FIELD

The present invention relates to a safety clasp and further to an improved clip for garments or clothing comprising that clasp. The invention elates particularly, but not exclusively, to a garment clip comprising that clasp for securing clothing or garments to a medical device, such as a catheter or feeding tube.

BACKGROUND

Many medical conditions or treatments require a patient to be fitted with a medical device for an extended period of time whether in a hospital or home setting. For example, commonly during illness and/or recovery patients require a feeding tube and or catheter to help support their system. As the patient moves, the catheter or other device tends to cause discomfort at the point of entry into the body due to the weight of the part of the device located outside of the patient's body.

In particular catheters are most often connected to other associated medical equipment that acts in concert with the catheter to deliver substances, collect substances and deliver energy or record information. Such devices are typically inserted into the body of a patient orally, nasally, intracutaneously or via the urethra. The discomfort is increased at the point where the catheter interfaces with the patient if the terminal end of the catheter is not restrained in some way, such as if the terminal end of the catheter is disconnected from associated medical equipment.

Furthermore catheters routinely require disconnecting from medical equipment while remaining fitted to a patient. The length of catheter remaining fitted to the patient can constitute a tripping or snagging hazard if it is not restrained in some way. The terminal end of the catheter can also act as a source of infection if left exposed and allowed to come into contact with non-sterile surfaces and can cause fluid leakage from the catheter. For example, a catheter inserted into the urethra of a male patient might contain a quantity of urine which, if the catheter was angled towards the floor, would empty.

The issue of loose and flexible wires, tubes or cables being difficult to secure on the human body is not unique to the medical field. For example conventional earphones or headphones used with a personal media player are connected to the media player by a cable. The cable splits into two at a point typically in the region of a person's chest. The media player might be located adjacent a person's waist or attached to a person's arm. The length of cable between the media player and the person's ears tends to urge the earphones or headphones downwardly and away from the person's ears. This can cause frustration, particularly when the person is active, i.e. running, where earphones can fall out of the person's ears frequently.

A clip suitable for receiving flexible cable or tubing (and thus can reversibly hold a medical device, such as a catheter, in that example) and attaching it securely to a person's or patient's clothing has been described in EP3331597. However, this clip and other similar attachment articles require a pin-based attachment to thread the clothing and secure the garment. Using sharp pins, even with a safety pin construction, adds to the potential risk for needle stick injury to the user or patient, which is particularly undesirable in the medical environment.

The present invention seeks to address this problem and the general problem of sharps risk when creating a secure attachment to garments, cloth or fabric.

SUMMARY

The present invention concerns a safety clasp comprising a clasp base; a securing element with a sharp end, a piercing section and a support; and a clasp body comprising first and second body sections and a recess defined therebetween, the body being adjustable relative to the clasp base and the securing element such that in an open configuration the recess is clear and only the first body section houses the sharp end and in a closed configuration the piercing section bridges the recess and only the second section houses the sharp end.

Usefully, when the clasp body is in an open configuration it may receive a garment or piece of cloth into the clasp, or release it from the clasp. This is because the two-part body defines a recess which is a gap or opening that the garment or cloth can be inserted or pushed into ready for securing. However, the sharp end of the securing element is not exposed to the user since the first part of the body keeps the sharp end covered, even in the clasp's open position and there is no risk of needle stick injury. Furthermore, once the garment is in the recess and ready to be secured, the clasp body can be adjusted by the user and is slidably moved along the clasp base into a closed position or configuration. When it is moved, the body pushes the fabric or cloth of the garment over the sharp end of the piercing section, impaling it onto the piercing section of the securing element. Once in the fully closed configuration the second part of the clasp body covers or protects the sharp end.

Thus, a key advantage of the invention is that its arrangement and operation means that there is no exposure of sharp end of the securing element to a user in either the open or closed configurations.

Further, since the securing element passes through the cloth of the garment, the clasp is able to take sufficient load to make it practically robust in use. As compared to standard garment fixing solutions, a relatively high load can be applied without deforming the clasp or causing it to open/fail. Provided the material through which it is passed is fairly strong the clasp will not detach (unless the material tears).

Advantageously, the clasp of the invention won't allow a user's finger to access a sharp end. In embodiments, the recess maybe between 3 and 4 mm in width and thus does not permit a person to accidentally catch their finger within the gap, preventing engagement at any time with the pointed end of the pin. Thus even though the safety clasp essentially uses a sharp end or pin structure, risk of injury is lowered significantly as access to the pointy or sharp end isn't possible with a finger, as it would be with traditional safety pins.

Further, the present safety clasp the arrangement overcomes variations in the surface properties of materials that during use would be faced by alternative 'gripping' types of fixture in order to satisfactorily secure clothing or a garment to a medical device.

Further, in some embodiments, the first and second body sections may define an inwardly tapered recess, which may be curved which guides the fabric towards an inwardly positioned apex between the first and second bodies.

In some embodiments the clasp base is the form of a rail, preferably a monorail, on which the clasp body is mounted and slidably adjustable between the open and closed positions. This provides a convenient and natural sliding mechanism by which the base and body operate relative to one another.

In some embodiments it is desirable that movement between open and closed configurations is limited or controlled to prevent accidental opening or closing of the clasp. This can be achieved by frictional movement or a mechanism to temporarily or reversibly retain the clasp in the open and closed configurations. In such arrangements the clasp is more secure. For example, the clasp base may comprise a mechanism configured to create friction and control the clasp body to stop it freely reciprocating between the open and closed positions. In particular, the clasp base and body may slidably operate together arranged as in a ratchet system such that movement is suitably controlled. Other systems designed to introduce a degree of control or friction may equally be utilised.

Alternatively, the clasp base may comprise a temporary non-return mechanism. For example, the base may comprise a spring board which biases upwardly into the clasp body in the open and/or closed position and thus is configured to releasably retain the body in that position until a minimal overriding force is provided by the user which overcomes the bias of the spring.

In preferred embodiments the securing element takes the form of a hooked pin which may be secured between the base of the clasp and a garment clip on to which the base is itself mounted.

In some examples one or both of the first and second body sections of the clasp body may further comprise a channel projecting inwardly from an upper internal ceiling surface. The channel of at least one section aligns with the piercing section and/or pointed end centrally within the body during reciprocal movement between the open and closed configurations. The first and second body sections may also comprise one or more gripping features, which may be in the form of apertures to allow the user to facilitate sliding of the clasp body between its open and closed configurations.

In a further embodiment, the invention extends to a garment clip the clip comprising a non-garment facing side and an opposing garment facing side, wherein the garment facing side comprises the safety clasp as disclosed herein.

In some examples, the clasp base may be reversibly mounted to the garment facing side of the clip or in other embodiments the base is moulded with or bonded to the garment facing side of the clip.

In some embodiments the support length of the securing element is arranged between the garment facing side of the clip and the clasp base such that the securing element is held firmly in position. The supporting length of the securing element maybe positioned under the base or in a space defined between where the rail is itself bonded to the garment facing side of the clip.

The garment clip of the invention is particularly suitable for attaching a flexible cable or tube to a garment. Usefully, the flexible cable or tube may be linked to a medical device or be part of a catheter and/or feeding tube.

As regards the non-garment facing side of the garment clip, the clip may comprise at least one receiving formation therein, the formation comprising a resiliently deformable channel for receiving a flexible cable or tube. In some examples two parallel longitudinal channels are provided.

In examples, the clip further provides flexible tabs are disposed adjacent to each of the two parallel longitudinal channels, each of said respective tabs being resiliently manoeuvrable to change the configuration of a respective one of the two parallel dimension and when in a second configuration the longitudinal channel has a second dimension, different to the first such that when in the second configuration a flexible tube or cable is permitted to enter the longitudinal channel and when in the first configuration the flexible tube or cable is restrained laterally within the longitudinal channel. The longitudinal channels may have a high friction surface, whereby longitudinal movement of the flexible cable or tube is resisted.

In some examples the body of the garment clip is formed from a high durometer thermoplastic elastomer and preferably a liner is formed from a low durometer thermoplastic elastomer.

To improve user handling, the clip may additionally comprise further a switch configured to operate the adjustment of the clasp body between open and closed positions. The switch may be more easily operable if the user can actuate between the open and closed positions without getting to the back side/garment facing side of the clip. Thus, in some embodiments the switch can be a pre-formed an extension of the clasp body which extends to an edge of the clip and thus arranged to permitting adjustment from the front or non-garment facing side of the clip. The switch may have a gripping feature such as serration or roughness to facilitate use.

In some embodiments the non-garment facing side of the body comprises at least one receiving formation therein, the formation comprising a resiliently deformable channel for receiving a flexible cable or tube. At least one of the two parallel longitudinal channels may comprise a high friction surface, whereby longitudinal movement of the flexible cable or tube is resisted.

The body of the garment clip may be formed from a high durometer thermoplastic elastomer such as Santoprene™. This offers several material properties which are advantageous to the present invention. Such a material is inherently flexible, thus reducing the risk of blunt or persistent trauma to the patient when the garment clip is being worn, by virtue of the compliant nature of the material, and has a high co-efficient of friction. Flexibility is important to enable the channels to deform thus permitting a cable or tube to enter and exit the channel. Friction is important to resist longitudinal movement of the cable or tube relative to the garment clip.

The body of the garment clip may alternatively be formed from a flexible thermoplastic such as polypropylene. The high friction surface in this case may be provided by a liner inserted into at least one of the two parallel longitudinal channels, said liner having a different coefficient of friction than the material of the body. The thickness of the liner may be in the range of 0.5-2 mm. The material of the liner may be for example a thermoplastic elastomer such as Santoprene™. A particularly desirable property of a low durometer grade of this material is that it provides substantial resistance to movement when placed in close contact with other materials even when the compressive forces applied are low. The combination of a more rigid body with a low durometer liner provides the advantage that it allows both compressive forces and surface friction affects to be independently optimised as each property is provided by a separate material.

Some applications may require two cables or tubes to be restrained longitudinally whereas other applications may require one, or no, cables or tubes to be restrained longitudinally. Different embodiments of garment clip can have different configurations of longitudinal channels having a high friction surface and/or low friction surface.

In some embodiments each of the two parallel longitudinal channels may have different dimensions to the other. In other embodiments each of the two parallel longitudinal channels may have substantially the same dimensions. The width of each of the two parallel longitudinal channels may be in the range of 2-4 mm. The length of each of the two parallel longitudinal channels may be in the range of 5-30 mm. The depth of each of the two parallel longitudinal channels may be in the range of 3-5 mm.

The garment clip may further comprise respective tabs are disposed adjacent to each of the two parallel longitudinal channels, each of said respective tabs being resiliently manoeuvrable to change the configuration of a respective one of the two parallel longitudinal channels wherein when in a first configuration the longitudinal channel has a first dimension and when in a second configuration the longitudinal channel has a second dimension, different to the first such that when in the second configuration a flexible tube or cable is permitted to enter the longitudinal channel and when in the first configuration the flexible tube or cable is restrained laterally within the longitudinal channel.

Provision of a flexible tab permits the body of the garment clip to be manoeuvred so as to change the dimensions of the longitudinal channels. When in a relaxed state a cable or tube held within a longitudinal channel is prevented from being removed laterally from the longitudinal channel. When the tab is flexed, the dimension of the longitudinal channel increases to enable a flexible cable or tube to laterally enter or exit the longitudinal channel.

BRIEF DESCRIPTION

Embodiments of the invention will now be described with reference to the following drawings.

DETAILED DESCRIPTION

Figure 1:
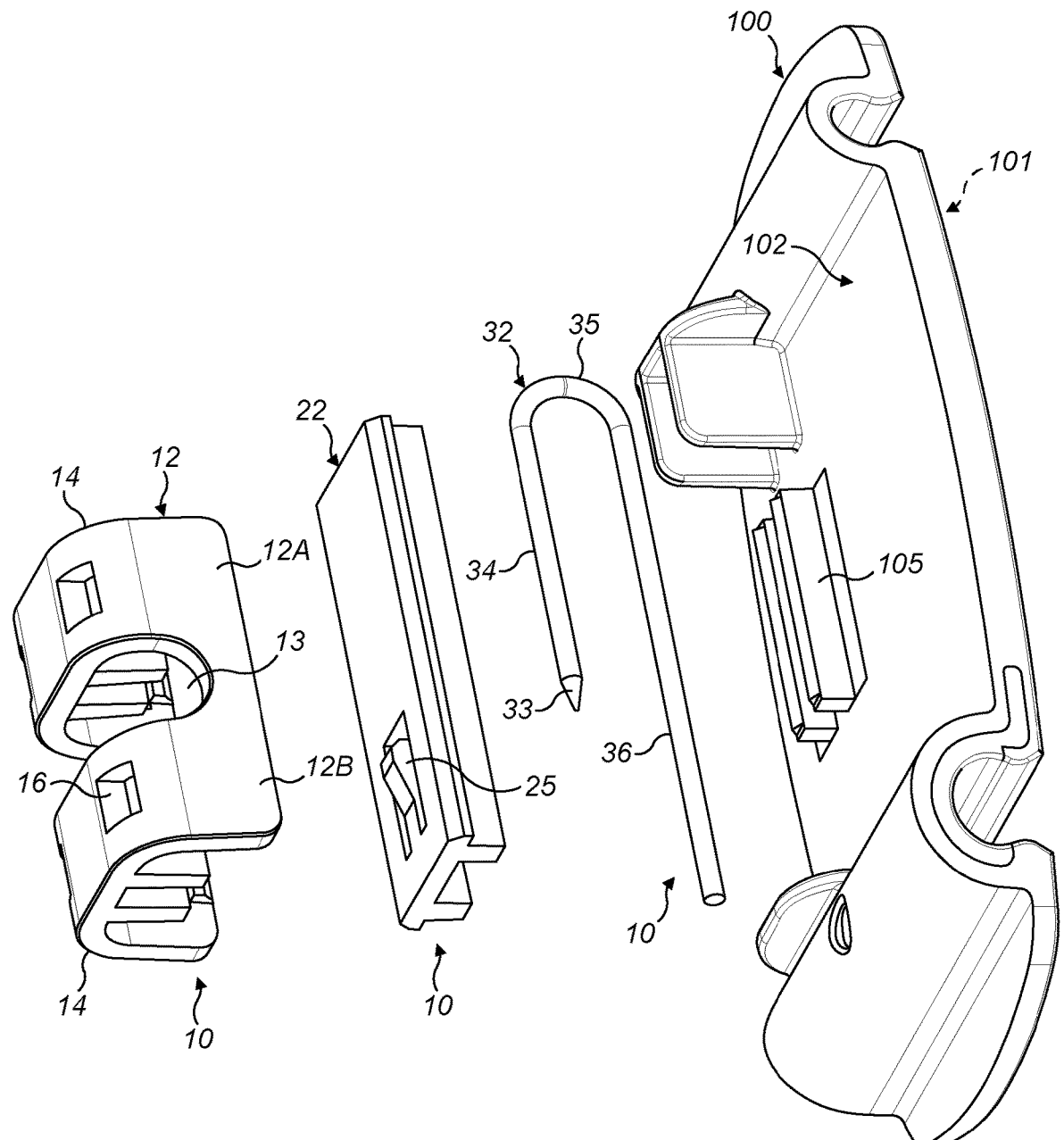
FIG. 1 illustrates an embodiment of the invention comprising of a garment clip and safety clasp, in exploded view.

FIG. 1 displays an exploded view of the unassembled components of one embodiment of the invention where a garment clip 100 may include a safety clasp 10. The safety clasp 10 comprises a clasp body 12, a clasp base 22 and a securing element 32. The body is generally hollow and comprises two parts or sections and is divided by a recessed or cut out portion 13 therebetween. The recess provides access to the internal part of the clasp body. The recess has a maximum width of 2.5 to 4 mm but is preferably around 3.5 mm and is graduated or tapered.

The body is divided in two sections: a first section 12A and a second section 12B. A cloth, fabric or garment may be inserted into the recess when it is required to be secured to the clip. The clasp body sections have flat upper external surface ceilings which are joined to the straight sides of the body by rounded upper surface corners 14. This further reduces/prevent user contact with sharp edges when operating the clasp. The corner sections 14 may have one or more gripping members 16 to allow the user to easily grasp and move/slide the clasp body. The internal surfaces of the straight sides of the body have channels 20 which allow the clasp body to be mounted on its clasp base 22.

The clasp body 12 further comprises clasp base 22. In this example the base is a monorail on to which the clasp body is mounted and arranged such that it may slide therealong. The base additionally includes a temporary non-return feature, shown as spring board 25, which will be explained in further detail below. The clasp also includes a securing element or pin 32. In this example the pin is arranged in a hooked shape and has a pointed end 33 with a piercing section 34 connected to a supporting length 36 by a curved section 35.

The garment clip 100 in the present embodiment is shown with features for attaching a flexible cable or tube to a garment. These will be discussed further below. The clip has a non-garment facing side 101 and an opposing garment facing side 102. The garment facing side 102 has a safety clasp 10 attached thereto, via the clasp base 22 of the safety clasp and which is aligned with and held to parallel longitudinal projections 105. The safety clasp acts to secure the garment clip 100 to garment worn by a person.

Figure 2:
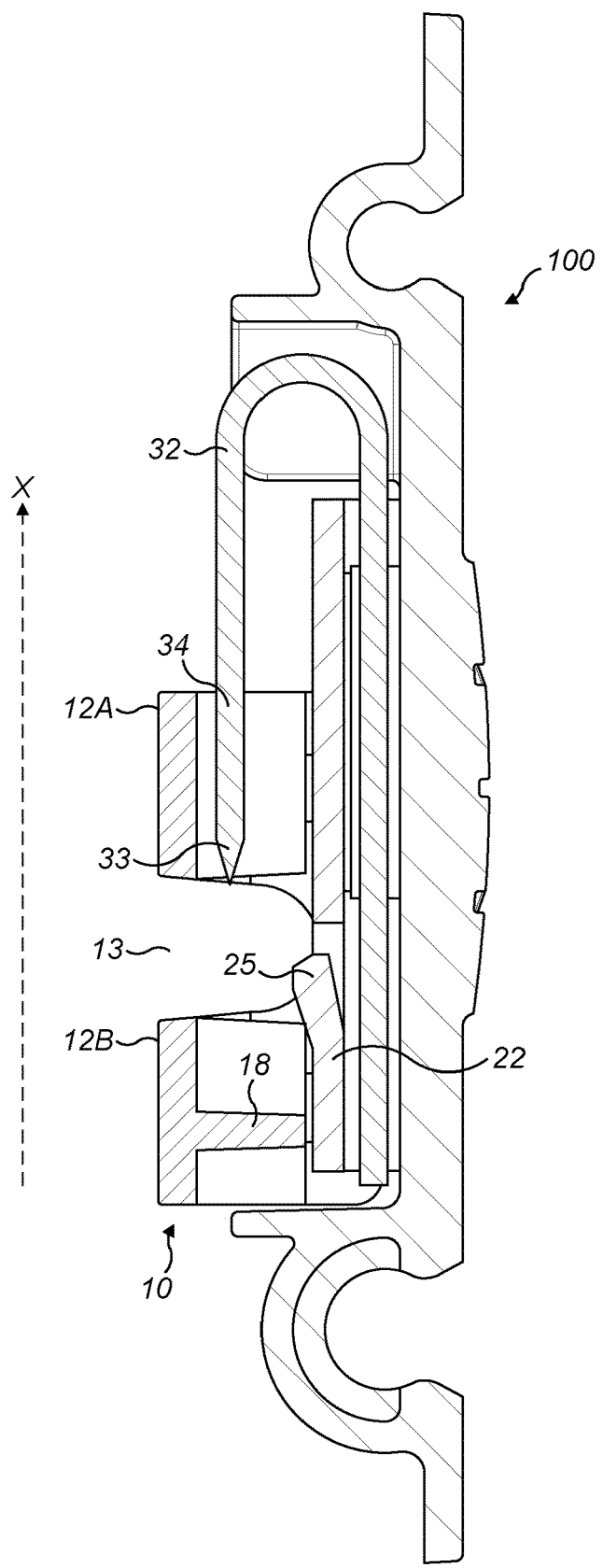
FIG. 2 illustrates an embodiment of the invention comprising an assembled garment clip having a safety clasp in an open configuration, in section view.
Figure 2A:
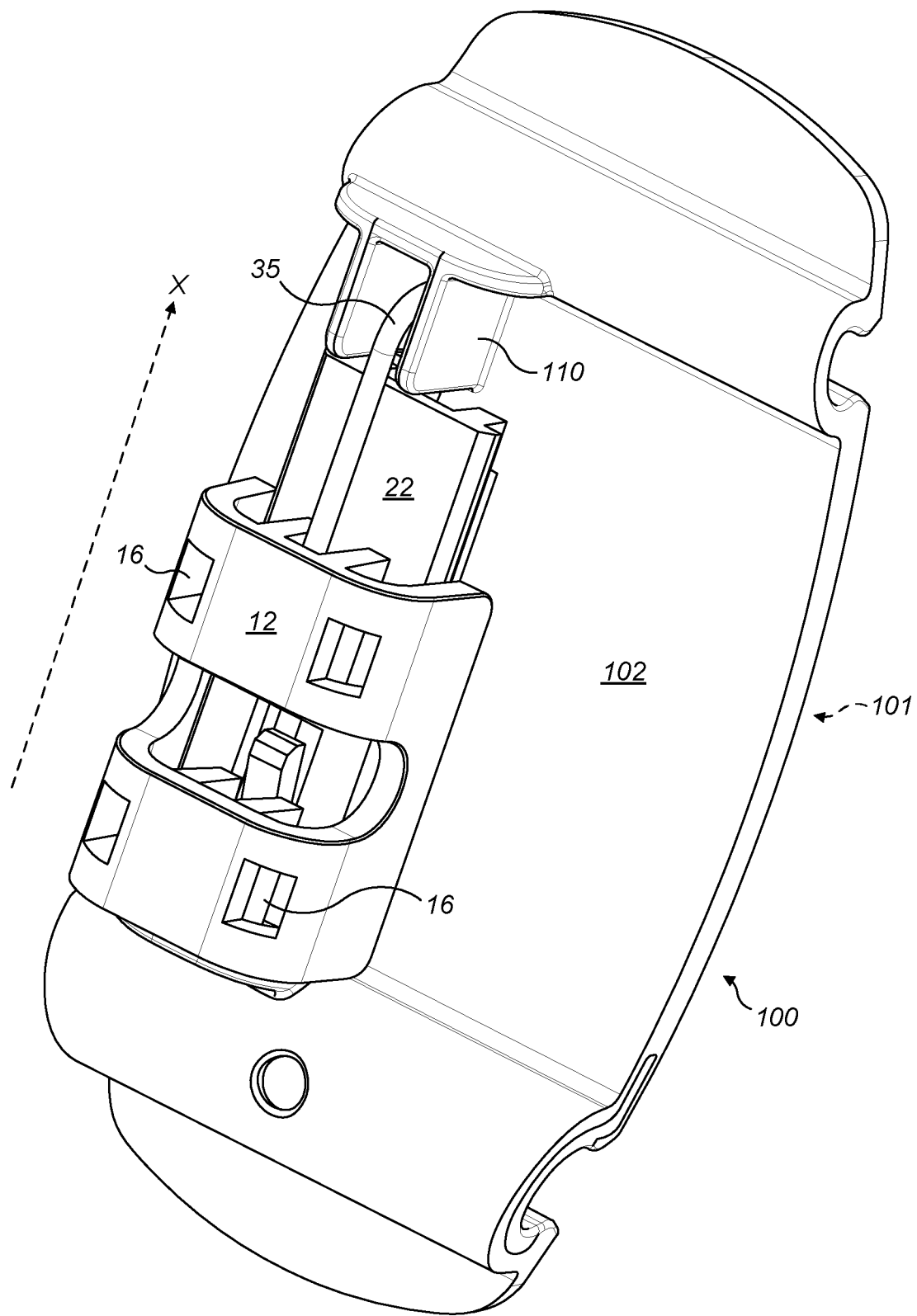
FIG. 2a illustrates the clip of FIG. 2, in perspective view.
Figure 2B:
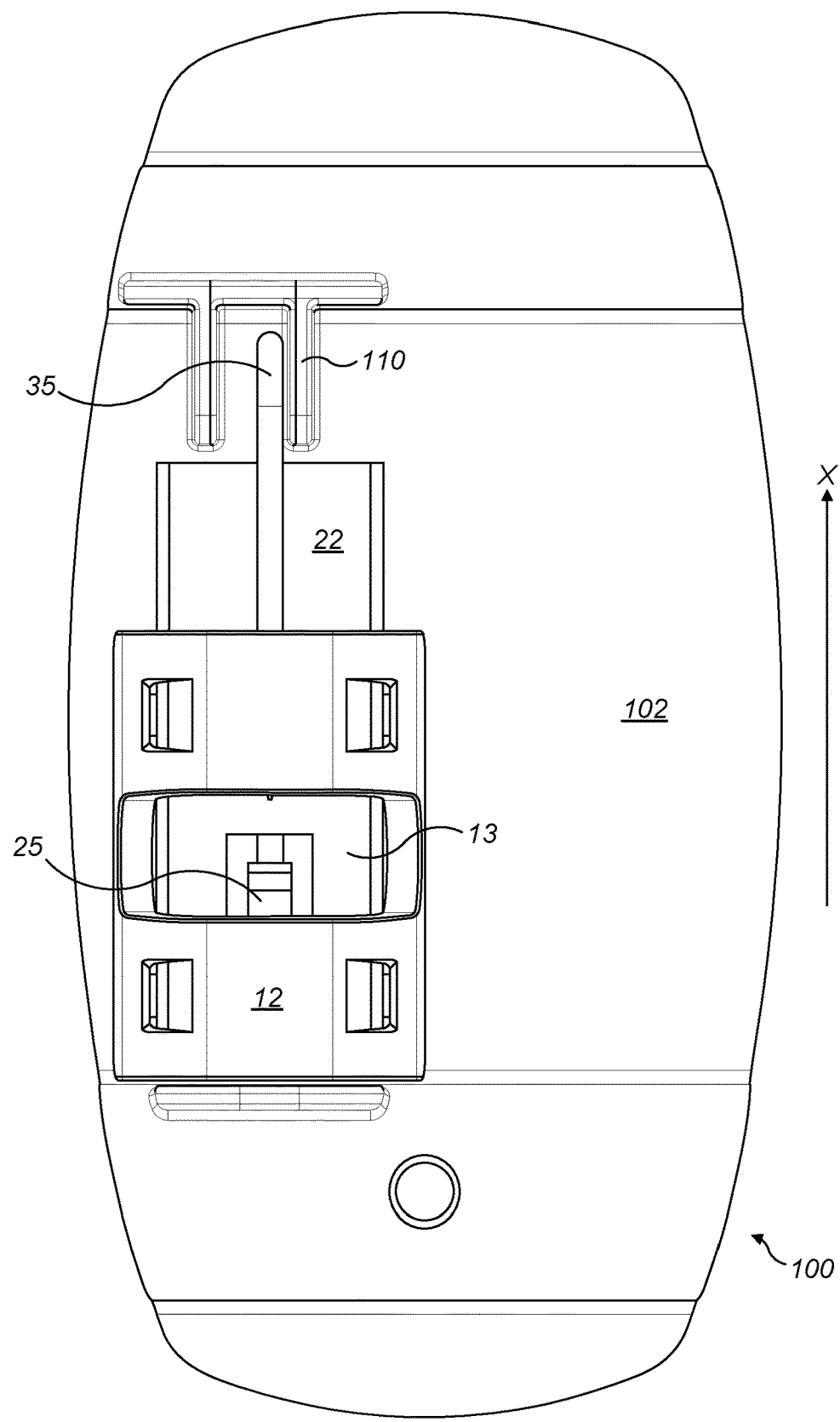
FIG. 2b illustrates the clip of FIG. 2, in plan view.

Referring to FIGS. 2a, 2b and 2c, the assembled garment clip 100 is shown in a series of different views, cross section, perspective and plan, respectively, to clearly display the features of the example.

The garment clip is shown with the safety clasp in its open configuration where the pointed end 33 of the piercing section of the securing member is covered by the first section 12A of the clasp body. The clasp body will not freely slide in this position but is releasably held by the spring board 25 of the base which projects upwardly into the internal space of the clasp body (as can be seen in FIGS. 2 and 2a particularly) and requires a light force in order to override the bias of the spring and slide the clasp body toward direction X. The clasp body 12 may be moved by the user by grasping gripping apertures 16. Here four apertures are shown, with one in each of the corners of the external surface of the clasp body. The garment facing side 102 of the garment clip 100 may further comprise a pin stall 110, in which the curved section 35 of pin 32 rests and is supported when assembled within the garment clip 100. As can be seen, in the open position the recess 13 is not blocked by the piercing section 33 of the pin and is thus configured to receive/release a garment from the clip.

Figure 3:
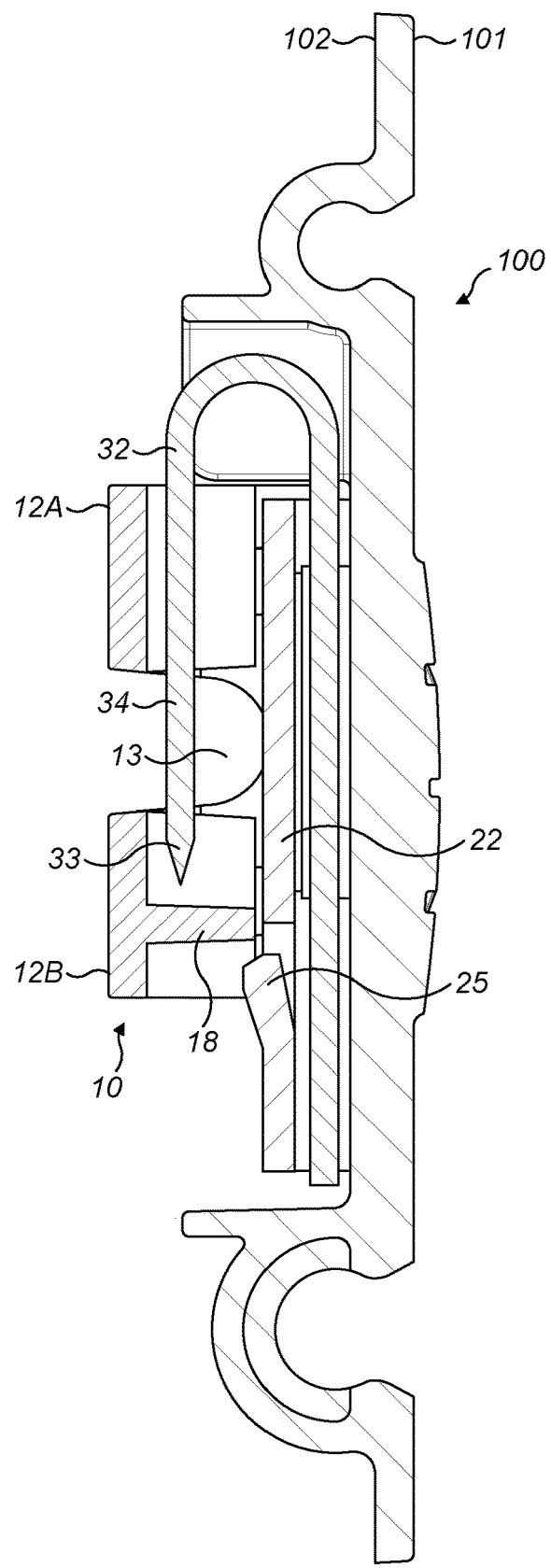
FIG. 3 illustrates an embodiment of the invention comprising an assembled garment clip having a safety clasp in the closed configuration, in section view.
Figure 3A:
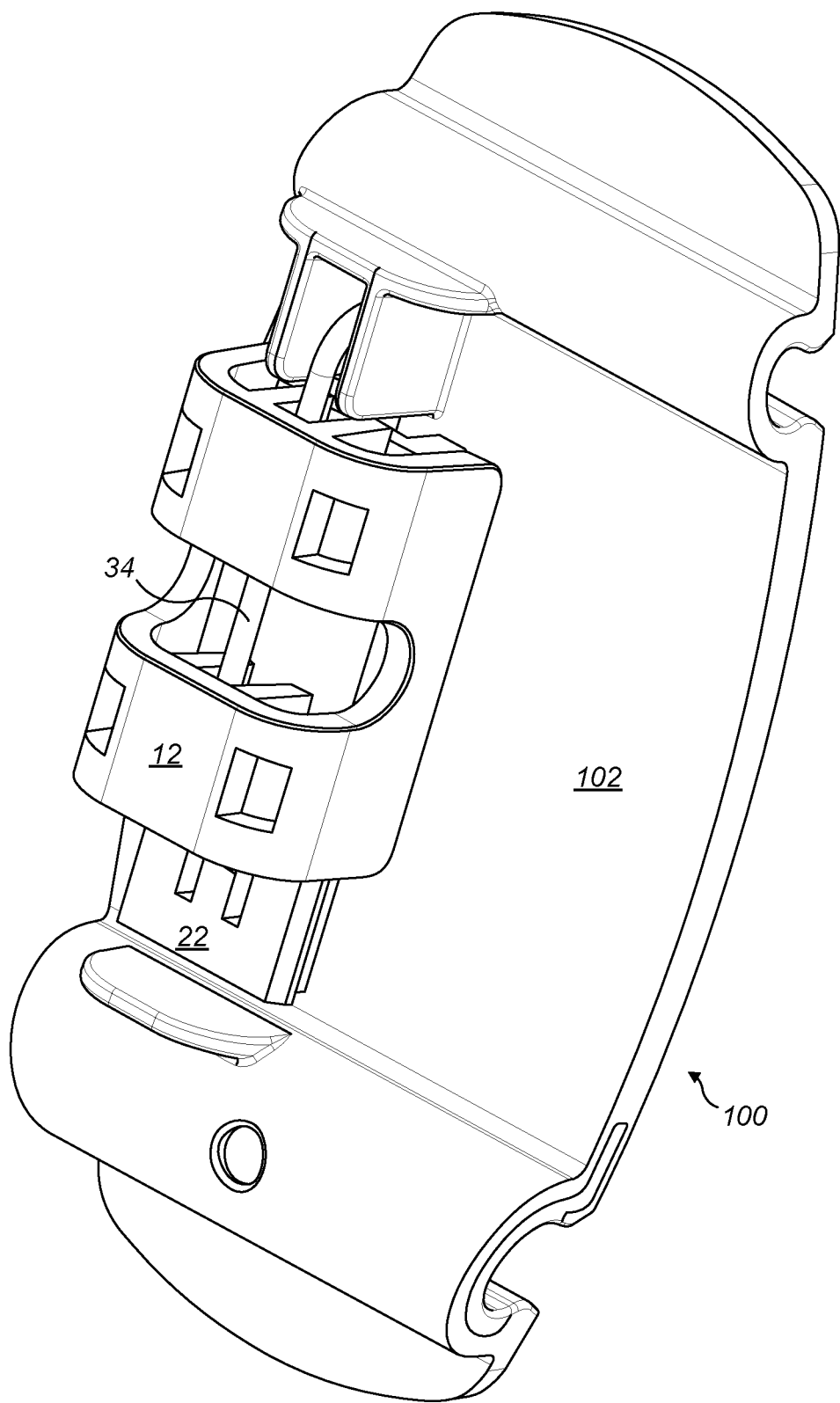
FIG. 3a illustrates the clip of FIG. 3, in perspective view.
Figure 3B:
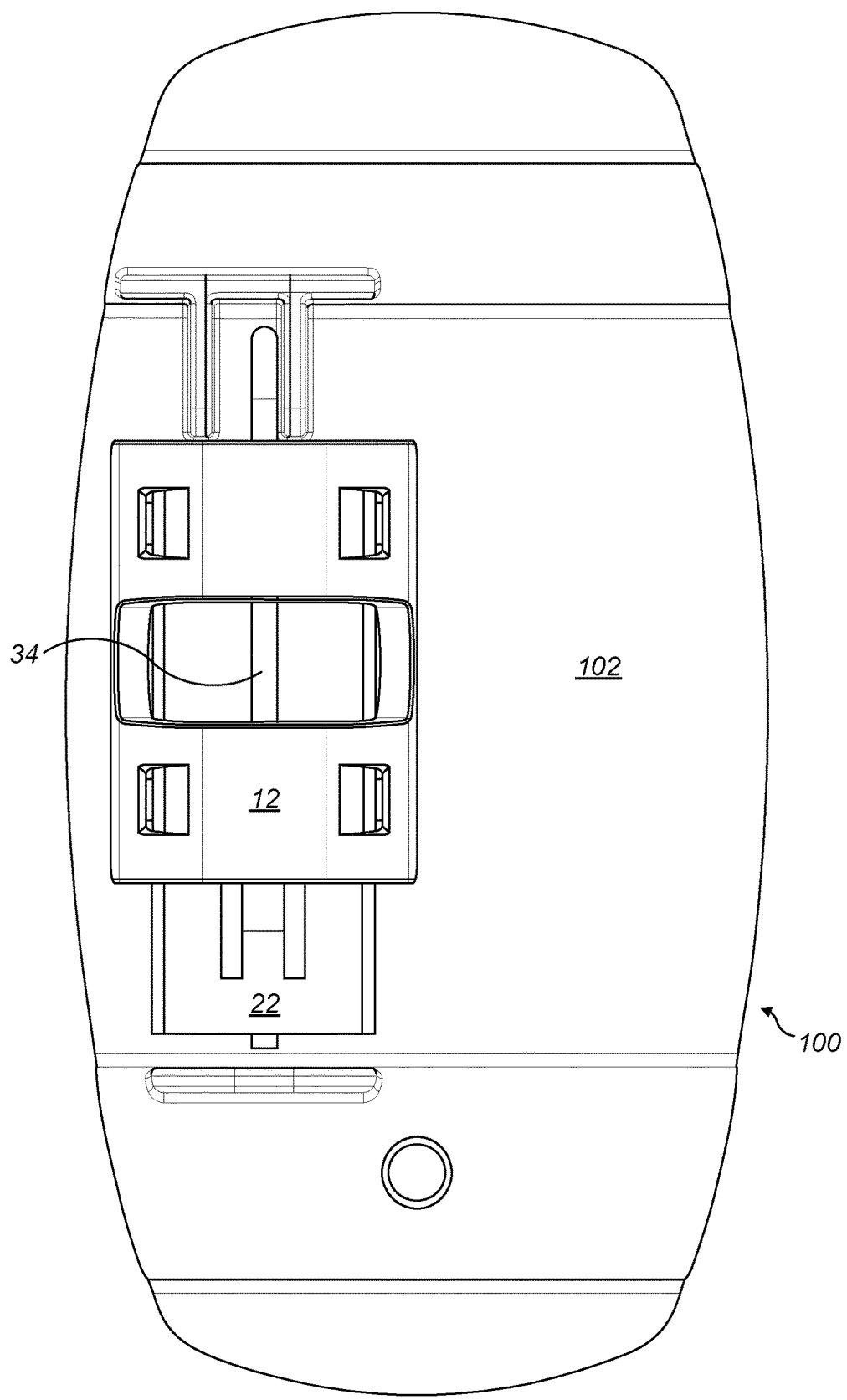
FIG. 3b illustrates the clip of FIG. 3, in a plan view.

As shown in FIGS. 3, 3a and 3b, the assembled garment clip 100 is shown in a series of different views: cross section, perspective and plan, respectively, to clearly demonstrate the arrangement of the features in this example. Here, the garment clip 100 is shown with the safety clasp 10 in its closed configuration. Here, the clasp body 12 has been slidably moved relative to the pin 32 and the base 22 within the garment clip; if fabric (not shown) of a garment is positioned within the recess when the garment clip is used, the sharp end 33 of the pin will have impaled the fabric and (being caught in the mechanism) the sharp end will have moved into the second section 12B of the clasp body via the recess space securing the fabric around the piecing section 34. The sharp end 33 rests, protected under the second section 12B of the clasp body 12. The user cannot access the sharp end 13 accidentally as the clasp body 12 has an internal barrier 18 within the second section 12B shielding the sharp end in its resting position. The piercing section 34 extends across the recess 13, bridging the gap between the first and second sections 12A, 12B. The clasp body will not freely slide from the closed position. The clasp body is releasably held by the spring board 25 of the base which projects upwardly from the plane of the clasp base 22 (as can be seen in FIG. 3 particularly) and requires a light force in order to override the bias of the spring and slide the clasp body back to its original open position.

Figure 4:
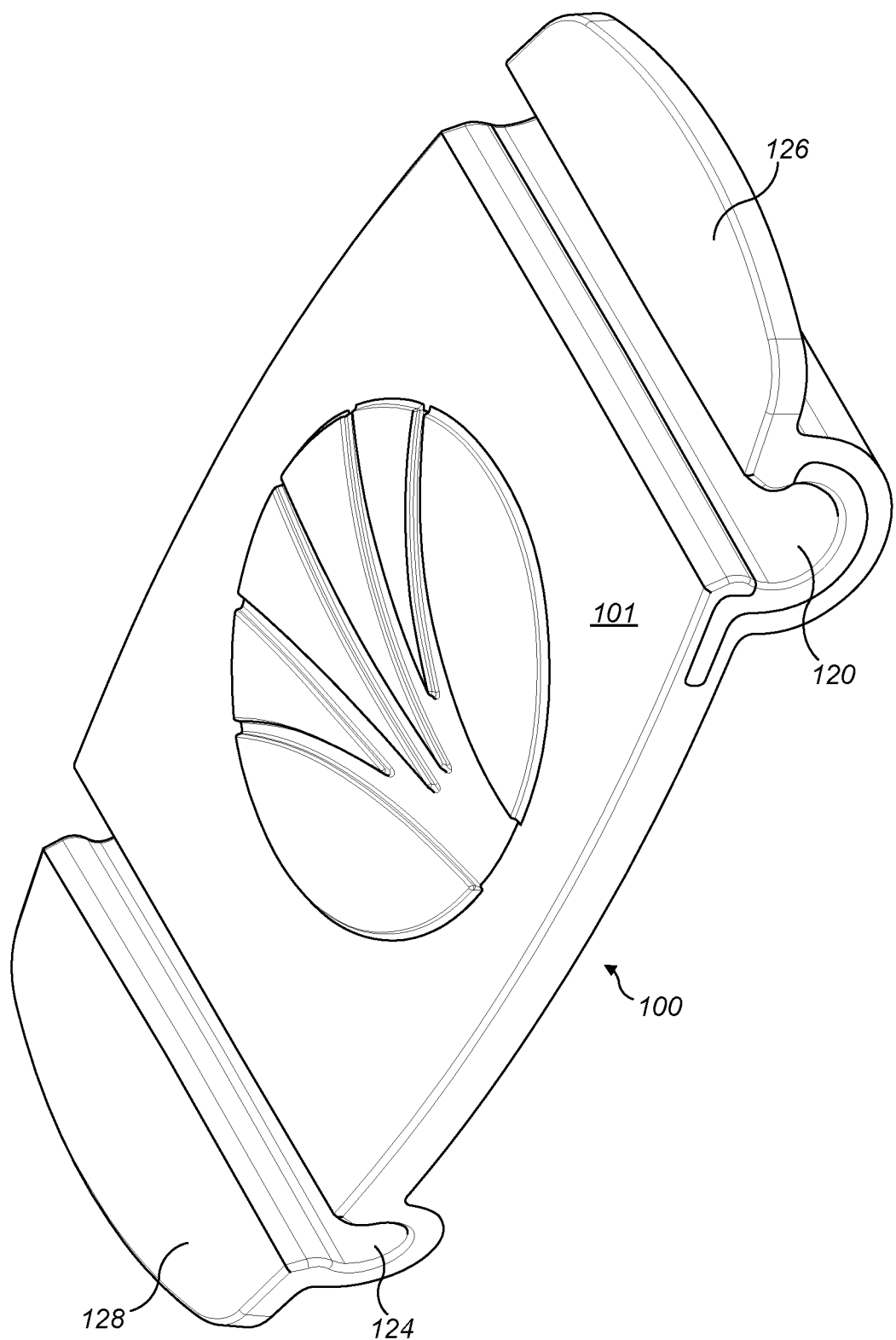
FIG. 4 shows a perspective view of the garment facing side of a garment clip according to a further embodiment of the invention.
Figure 4A:
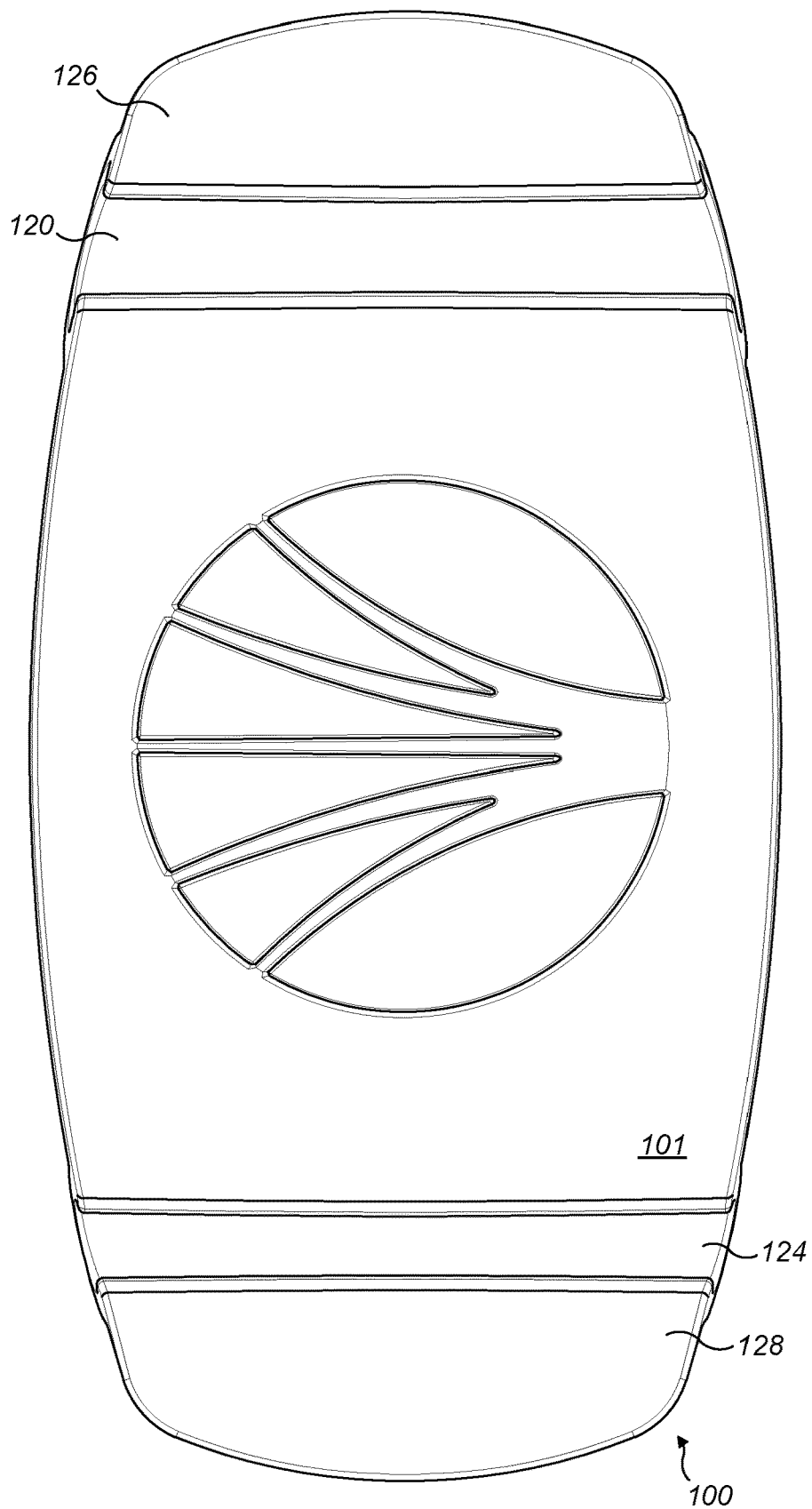
FIG. 4a shows the garment clip of FIG. 4 in plan view.

FIGS. 4 and 4a show an embodiment of the garment clip 100 showing in particular the non-garment facing side 101 which acts to secure a flexible cable or tube to a garment, for example the tube of a medical device such as a catheter.

In this example, two deformable channels 120, 124 are formed in a parallel relationship on the non-clothing/garment side, but it will be appreciated that other embodiments may include just one deformable channel or more than two deformable channels arranged in other positions. In the illustrated embodiment, one longitudinal channel 120 may have a width of 2.6 mm, depth of 3.6 mm and length of 22 mm. A flexible tab 126, 128 is positioned outwardly adjacent to each of the parallel longitudinal channels 120, 124. Each flexible tab 126, 128 is biased in a first position, substantially planar with the surface of the garment clip 100.

If formed from a flexible thermoplastic elastomer, the garment clip 100 can provide flexibility for a cable or tube to be inserted into each deformable channel 120, 124, whilst also being safely attached to a patient or user. The material also provides friction between the cable or tube and garment clip 100 to assist in preventing movement of the cable or tube relative to the garment clip 100.

Examples of suitable materials include a high durometer Santoprene™. Alternatively and preferentially the body of the clip is formed from a more rigid thermoplastic such as polypropylene and one or more of the deformable channels 120, 124 may be lined with a different material. Such a liner may resist or encourage longitudinal movement of a flexible tube or cable within the deformable channel.

In use, a part of a catheter or flexible cable is inserted into a deformable channel 120, 24 by applying a force to the flexible tab 126, 128 so as to deform the flexible body of the clip and open the longitudinal channel 120, 124 to permit lateral entry of a flexible cable or tube. The flexible tab 126, 128 is then released to close and compressive holding forces prevent lateral exit of a flexible cable or tube from the longitudinal channel. The flexible cable or tube cannot then easily be removed laterally from the deformable channel thereby usefully reversibly securing the cable or tube to the garment clip on the non-garment side. Usefully, the garment clip can then be secured to a garment via the actions described in relation to opening and closing the safety clasp on the garment/clothing facing side.

The invention claimed is:

1. A safety clasp comprising:
   a clasp base;
   a securing element with a sharp end, a piercing section and a support; and
   a clasp body comprising first and second body sections and a recess defined therebetween, the clasp body being mounted on and configured to slide relative to the clasp base and the securing element such that in an open configuration the recess is clear and only the first body section houses the sharp end and in a closed configuration the piercing section bridges the recess and only the second body section houses the sharp end.

2. The safety clasp according to claim 1, wherein the clasp base is the form of a rail on which the clasp body is mounted and slidably adjustable between the open and closed configurations.

3. The safety clasp according to claim 1, wherein the clasp base comprises a ratchet configured to control the clasp body reciprocating between the open and closed configurations.

4. The safety clasp according to claim 1, wherein the clasp base comprises a spring board configured to releasably retain the clasp body in the open configuration or the closed configuration.

5. The safety clasp according to claim 1, wherein the securing element is a hooked pin.

6. The safety clasp according to claim 1, wherein the first and second body sections define an inwardly tapered recess.

7. The safety clasp according to claim 1, wherein one or both of the first and second body sections further comprises an internal channel arranged to surround the piercing section and/or sharp end of the securing element.

8. The safety clasp according to claim 1, wherein an external surface of the clasp body has one or more gripping features.

9. A garment clip comprising a non-garment facing side and an opposing garment facing side, wherein the garment facing side comprises the safety clasp of claim 1.

10. The garment clip according to claim 9, wherein the clasp base is reversibly mounted to the garment facing side of the clip, or is moulded with, or bonded to, the garment facing side of the clip.

11. The garment clip according to claim 9, wherein the support of the securing element is fixed against the garment facing side of the clip by the clasp base.

12. The garment clip according to claim 9, wherein the garment clip is for attaching a flexible cable or tube and the non-garment facing side of the body comprises at least one receiving formation therein, the receiving formation comprising a resiliently deformable channel for receiving a flexible cable or tube.

13. The garment clip according to claim 12, wherein the at least one receiving formation comprises two parallel longitudinal channels.

14. The garment clip according to claim 13, wherein respective tabs are disposed adjacent to each of the two parallel longitudinal channels, each of said respective tabs being resiliently manoeuvrable to change a configuration of a respective one of the two parallel longitudinal channels, wherein the respective one of the longitudinal channels has a first dimension in a first configuration such that the flexible tube or cable is restrained laterally within the longitudinal channel and a second dimension in a second configuration such that the flexible tube or cable is permitted to enter the longitudinal channel.

15. The garment clip according to claim 13, wherein at least one of the two parallel longitudinal channels comprises a high friction surface, whereby longitudinal movement of the flexible cable or tube is resisted.

16. The garment clip according to claim 9, wherein the body of the garment clip is formed from a high durometer thermoplastic elastomer, the garment clip further comprising a liner formed from a low durometer thermoplastic elastomer.

17. The garment clip for attaching a flexible cable or tube to clothing according to claim 12, wherein the flexible cable or tube is a catheter and/or feeding tube.

18. A garment clip comprising:
   a first side configured to face a fabric to be secured to the garment clip, and a second side opposite the first side along a thickness of the garment clip, the second side being configured to face away from the fabric; and
   a safety clasp comprising:
      a clasp base secured to the first side,
      a securing element comprising a sharp end, a support portion opposite the sharp end along a length of the securing element, and a piercing portion therebetween, the support portion being secured to the first side, and
   a clasp body extending from a first end to a second end along a length of the clasp body, the clasp body comprising a first portion, a second portion opposite the first portion along the length of the clasp body, an opening defined between the first and second portions along the length of the clasp body, and a channel defined by the first and second portions and extending at least partially along the length of the clasp body, the opening being configured to receive the fabric therein, wherein the clasp body is positioned over the clasp base and the securing element with the sharp end of the securing element positioned within the channel, the clasp body being configured to slide over the clasp base and the securing element between (i) an open configuration in which the sharp end is positioned within the channel at the first portion of the clasp body, and (ii) a closed configuration in which the sharp end is positioned within the channel at the second portion of the clasp body and the piercing portion extends through the opening.

19. The garment clip of claim 18, wherein the channel is closed at the second end of the clasp body.

20. The garment clip of claim 18, further comprising two projections extending from the first side, and wherein the two projections secure at least one of the clasp base or the support portion of the securing element to the first side.

\* \* \* \* \*